United States Patent
Han et al.

(10) Patent No.: US 9,194,778 B2
(45) Date of Patent: Nov. 24, 2015

(54) COMPOSITIONS AND KITS FOR SEPARATING CELLS AND METHOD OF SEPARATING CELLS USING THE SAME

(71) Applicant: Samsung Electronics Co., Ltd., Suwon-si, Gyeonggi-do (KR)

(72) Inventors: Kyung-yeon Han, Seoul (KR); Yeon-jeong Kim, Yongin-si (KR); Jong-myeon Park, Incheon (KR); Chang-eun Yoo, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 13/868,824

(22) Filed: Apr. 23, 2013

(65) Prior Publication Data

US 2014/0162281 A1 Jun. 12, 2014

(30) Foreign Application Priority Data

Dec. 6, 2012 (KR) ........................ 10-2012-0141199

(51) Int. Cl.
*G01N 33/53* (2006.01)
*G01N 1/34* (2006.01)
*G01N 33/543* (2006.01)
*G01N 33/574* (2006.01)

(52) U.S. Cl.
CPC ............ *G01N 1/34* (2013.01); *G01N 33/54326* (2013.01); *G01N 33/574* (2013.01)

(58) Field of Classification Search
None
See application file for complete search history.

(56) References Cited

U.S. PATENT DOCUMENTS

| | | | |
|---|---|---|---|
| 2003/0147886 A1* | 8/2003 | Thomas et al. | 424/144.1 |
| 2003/0216317 A1* | 11/2003 | Ohba et al. | 514/12 |
| 2007/0207508 A1 | 9/2007 | Yao et al. | |
| 2009/0110753 A1* | 4/2009 | Dubois et al. | 424/649 |
| 2010/0015727 A1* | 1/2010 | Cui | 436/518 |
| 2010/0255479 A1 | 10/2010 | Mikolajczyk et al. | |
| 2010/0273160 A1* | 10/2010 | Donahoe et al. | 435/6 |
| 2012/0071335 A1 | 3/2012 | Manaresi et al. | |
| 2012/0100538 A1 | 4/2012 | Mikolajczyk et al. | |

FOREIGN PATENT DOCUMENTS

| | | |
|---|---|---|
| JP | 2008-102012 A | 1/2008 |
| JP | 2010-045996 A | 4/2010 |

OTHER PUBLICATIONS

Nokleb et al. (Introgen Lab Notes 2008).*
Piao et al. (Analyst 2009 vol. 134, p. 926-932).*
Aktas et al., "Stem Cell and Epithelial-Mesenchymal Transition Markers are Frequently Overexpressed in Circulating Tumor Cells of Metastatic Breast Cancer Patients," *Breast Cancer Research*, 11(4): 1-9 (2009).
Reya et al., "Stem Cells, Cancer, and Cancer Stem Cells," *Nature*, 414: 105-111 (2001).
Mani et al., "The Epithelial-Mesenchymal Transition Generates Cells with Properties of Stem Cells," *Cell*, 133: 704-715 (2008).
Al-Hajj et al., "Therapeutic Implications of Cancer Stem Cells," *Current Opinion in Genetics & Development*, 14: 43-47 (2004).
CTRC-AACR San Antonio Breast Cancer Symposium, Newsletter 5 Brochure, (Dec. 8-12, 2010).
Kasimir-Bauer et al., "Expression of stem cell and epithelial-mesenchymal transition markers in primary breast cancer patients with circulating tumor cells", *Breast Cancer Research*, 14 (R15): 1-9 (2012).

* cited by examiner

*Primary Examiner* — Jacob Cheu
(74) *Attorney, Agent, or Firm* — Leydig, Voit & Mayer, Ltd.

(57) ABSTRACT

Provided are compositions, kits, and methods for separating cells including complexes of at least one type of linker capable of binding to an antibody or antigen binding fragment and a solid phase.

5 Claims, 2 Drawing Sheets

COMPOSITIONS AND KITS FOR SEPARATING CELLS AND METHOD OF SEPARATING CELLS USING THE SAME

CROSS-REFERENCE TO RELATED APPLICATIONS

This application claims the benefit of Korean Patent Application No. 10-2012-0141199, filed on Dec. 6, 2012 in the Korean Intellectual Property Office, the disclosure of which is incorporated herein in its entirety by reference.

BACKGROUND

1. Field

The present disclosure relates to compositions, kits, and methods for separating cells including complexes of at least one type of linker and a solid phase.

2. Description of the Related Art

Cancer stem cells (CSCs) are genetically mutated cells that divide indefinitely and are capable of giving rise to cancer cells with various phenotypes. CSCs exist in small quantities in cancerous tissue and may induce treatment-resistance, cancer recurrence, and cell transformation. However, markers and expressed proteins of CSCs are not well characterized.

Epithelial mesenchymal transition (EMT) occurs when cells transform from an epithelial cell phenotype into a highly mobile mesenchymal cell phenotype. Usually, this process is part of normal embryonic development. However, irreversible EMT may contribute to the development of heart, liver, kidney, or blood vessel problems, or to the transformation of a normal cell into a malignant tumor cell. EMT involves a loss of polarity between apical surface and basal cell surfaces, a cell shape change from a square shape to a fibroblast shape, a decrease in epithelial cell markers, and an increase in mesenchymal cell markers. EMT plays various roles in tissue regeneration, fibrosis, cancer development, and cell transformation other than in prenatal tissue development and differentiation.

Circulating tumor cells (CTCs) are tumor cells present in blood and are known to contribute to cancer metastasis.

However, it is difficult to quantify CSCs, cells that have undergone EMT, and CTCs because these types of cells are fragile and exist in small quantities.

Accordingly, a highly sensitive diagnostic method of detecting these target cells is still required.

SUMMARY

Provided are compositions for separating cells.
Provided are kits for separating cells.
Provided are methods of separating cells.
Provided are compositions for separating cells including complexes of at least one type of linker capable of binding to an antibody or antigen binding fragment and a solid phase.

The term "antibody" is used interchangeably herein with the term "immunoglobulin (Ig)". A complete antibody has two full-length light chains and two full-length heavy chains, and each light chain binds to each heavy chain by a disulfide bind (S-S bind). The antibody may be, for example, IgA, IgD, IgE, IgG, or IgM.

The term "antigen binding fragment" as used herein refers to a fragment of a complete immunoglobulin, or a part of a polypeptide including a site where an antigen may bind. The antigen binding fragment may be, for example, $F(ab')_2$, Fab', Fab, Fv, or scFv. Fab has a structure including a light chain variable region, a heavy chain variable region, and a first constant region ($C_{H1}$) of the heavy chain. Also, Fab has one antigen binding site. Fab' is different from Fab in that Fab' has a hinge region including at least one cysteine residue at a C-terminal of the $C_{H1}$ domain of the heavy chain. $F(ab')_2$ antibody is produced by an S-S binding between the cysteine residues of the hinge region of the Fab'. Fv is a minimal antibody fragment only having the heavy chain variable region and the light chain variable region. Methods of forming an Fv fragment is known to one of ordinary skill in the art. A two-chain Fv has a non-covalent bond between the heavy chain variable region and the light chain variable region, and a single-chain Fv (scFv) generally has a covalent bond by a peptide linker between the heavy chain variable region and the light chain variable region. A scFv may also form a dimer structure as in a two-chain Fv by directly binding the heavy chain variable region and the light chain variable region at the C-terminals thereof. The antigen binding fragment may be prepared using a protein hydrolase, and may be prepared by recombinant DNA technology. For example, Fab may be obtained by restriction fragmenting of the complete antibody using papain and $F(ab')_2$ fragment may be obtained by fragmenting the complete antibody using pepsin.

The antibody or the antigen binding fragments may be antibodies or antigen binding fragments from at least two types of different host species. The host species may be, for example, a mouse, a rat, a rabbit, a goat, a guinea pig, or a human.

The term "linker" as used herein refers to a material that connects an antibody or antigen binding fragment with a material, such as a bead. The linker may be, for example, a nucleic acid, a protein, a polypeptide, a polymer, or a combination thereof. The linker may have a binding affinity for the antibody or antigen binding fragment. The linker may be, for example, protein A, protein G, protein NG, protein L, anti-immunoglobulin antibody, Jacalin, or a combination thereof. Protein A is a 55 kDa protein present on a cell wall of *Staphylococcus aureus*. Protein A binds with a high binding affinity to mouse IgG2a, mouse IgG2b, human IgG1, and human IgG2, and binds with an intermediate binding affinity to mouse IgG3, mouse IgG1, human IgM, human IgA, and human IgE. Protein G is an immunoglobulin binding protein expressed in a group C or a group G *Staphylococcus* bacteria. Protein G may bind to a wider range of animal types or to a wider range of IgG subunits. Protein NG refers to a recombinant fusion protein prepared by combining IgG binding domains of protein A and protein G. Protein NG may bind to all subclasses of human IgG, and may bind to human IgA, human IgE, human IgM, and human IgD. In addition, protein NG may bind to all subclasses of mouse IgG. Protein L is a protein separated from a surface of a *Peptostreptococcus magnus* bacterium. In contrast to protein A and protein G binding to an Fc region of the immunoglobulin, protein L binds to the immunoglobulin by a light chain interaction. Because protein L does not bind to the heavy chain of the immunoglobulin, protein L binds to a wider range of antibodies than protein A or protein G. Protein L binds to all types of antibodies including IgG, IgM, IgA, IgE, and IgD, and protein L also binds to scFv and Fab. Jacalin is a plant lectin found in jackfruit. Jacalin may bind to an O-glycoprotein such as mucins and IgA1. The term "anti-immunoglobulin antibody" is used interchangeably herein with the term "anti-antibody" or with the term "secondary antibody." An anti-immunoglobulin antibody is a protein that binds to an antibody or an antibody fragment, such as a Fc region or a Fab region.

The term "solid phase" (or "solid support") as used herein refers to a stationary phase in chromatography. With respect to column chromatography, the solid phase is an adsorbent (solid) filled in a separating tube or a liquid impregnated on a carrier. With respect to paper chromatography, the solid phase is a liquid maintained in a carrier such as a filter paper and the like. With respect to affinity chromatography, the solid phase may be a material having an adsorbent that is bound to a compound having a specific affinity to a target material. The solid phase may be, for example, a magnetic bead, a polystyrene plate, or a polystyrene bead.

A complex of a linker and a solid phase refers to a linker bound to a solid phase. The linker and the solid phase may be bound physically or chemically.

The cells may be, for example, cancer cells, cancer stem cells (CSCs), circulating tumor cells (CTCs), cells that have undergone an epithelial mesenchymal transition (EMT), or a combination thereof. A cancer cell may originate from, for example, liver cholangiocarcinoma, liver cancer, thyroid cancer, colon cancer, testis cancer, myelodysplastic syndrome, glioblastoma, oral cavity cancer, fungoid mycosis, acute myeloid leukemia, chronic myeloid leukemia, acute lymphocytic leukemia, chronic lymphocytic leukemia, basal cell cancer, ovarian epithelial cancer, ovarian germ cell tumor, male breast cancer, encephaloma, pituitary adenoma, multiple myeloma, gallbladder cancer, biliary tract cancer, colorectal cancer, retinoblastoma, choroidal melanoma, ampulla vater, bladder cancer, peritoneal cancer, parathyroid cancer, adrenal cancer, non-small cell lung cancer, tongue cancer, astrocytoma, small cell lung cancer, pediatric brain tumor, pediatric lymphoma, pediatric leukemia, small bowel neoplasm, meningioma, esophageal cancer, glioma, neuroblastoma, ureter cancer, renal cell carcinomoa, malignant soft tissue tumor, malignant bone tumor, malignant lymphoma, malignant mesothelioma, malignant melanoma, eye melanoma, pudendum cancer, urethral cancer, carcinoma of unknown primary origin, gastric lymphoma, stomach cancer, gastric carcinoid tumor, gastrointestinal stromal tumor, Wilm's tumor, breast cancer, sarcoma, penile cancer, pharynx cancer, gestational trophoblatsic disease, uterine cervical cancer, endometrial cancer, uterus sarcoma, prostate cancer, metastatic brain tumor, rectal cancer, rectal carcinoid tumor, vaginal cancer, spinal cord tumor, vestibular schwannoma, pancreatic cancer, salivary gland tumor, tonsillar cancer, squamous cell carcinoma of lung, adrenocarcinoma of lung, lung cancer, lung squamous cell carcinoma, skin cancer, anal cancer, larynx cancer, or a combination thereof.

CSCs are genetically mutated cells that divide and/or proliferate indefinitely and are capable of giving rise to cancer cells with various phenotypes. CTCs are tumor cells present in blood and are known to contribute to cancer metastasis. Cells that have undergone EMT may be, for example, CTCs.

Provided are kits for separating cells including complexes of at least one type of linker that specifically binds an antibody or antigen binding fragment to a solid phase.

The antibody, the antigen binding fragment, the linker, the solid phase, the complex, and the cells are the same as described above.

A kit may further include a material for separating the solid phase. The kit may further include, for example, a buffer or a magnet.

Provided are methods of separating cells, the methods including incubating a sample comprising a target cell and an antibody or antigen binding fragment to prepare a first complex of the target cell and the antibody or antigen binding fragment; incubating the first complex with a second complex of at least one type of linker capable of binding to the antibody or the antigen binding fragment and a solid phase, to prepare a third complex of the target cell, the antibody or the antigen binding fragment, the linker, and the solid phase; and separating the target cell from the third complex. The antibody, the antigen binding fragment thereof, the linker, the solid phase, the complex, and the cells are the same as described above.

The method includes incubating a sample including a target cell and an antibody or antigen binding fragment to prepare a first complex of a target cell and an antibody or antigen binding fragment.

The antibody or antigen binding fragment may be a free antibody or antigen binding fragment that is not bound to the solid phase. The free antibody or antigen binding fragment is bound to the target cell. Herein, the linker may bind the antibody or antigen binding fragment to form a complex including the target cell, the antibody or antigen binding fragment, the linker, and the solid phase. Because the binding is mediated by the linker, the binding may be referred to as "indirect binding". In contrast, when the target cells are separated using antibodies or antigen binding fragments bound directly to the solid phase, the binding may be referred to as "direct binding." Because the free antibodies or antigen binding fragments bind to the target cell in indirect binding, an antigen binding efficiency and cell separation efficiency is high compared to direct binding.

The term "target cells" refers to cells to be separated or detected.

The sample may be tissue, blood, bone marrow, lymph, saliva, lachrymal fluid, urine, mucous, amniotic fluid, or a combination thereof.

The incubating may be performed, for example, in vitro.

The first complex may be, for example, a complex of the target cell and the antibody, or a complex of the target cell and the antigen binding fragment.

The method includes incubating the first complex with a second complex of at least one type of linker capable of binding to an antibody or antigen binding fragment and a solid phase, to prepare a third complex including the target cell, the antibody or antigen binding fragment, the linker, and the solid phase.

The second complex refers to a material wherein the linker and the solid phase are bound. The linker and the solid phase may bind physically or chemically.

The incubating may be performed, for example, in vitro.

The third complex refers to a material wherein the first complex and the second complex are bound. The first complex and the second complex may bind physically or chemically.

The method includes separating the target cell from the third complex.

In the method, the binding affinity to the antibody or the antigen binding fragment varies depending on the type of the linker. The antibody or antigen binding fragment may be selected according to a host species or subclasses of the antibody or antigen binding fragment. Hence, when the type of the linker varies, the antibody or antigen binding fragment may be selected, and as a result, the target cells may be selectively separated. For example, when a mouse antibody and a rabbit antibody are incubated in the sample, and an anti-mouse Ig is used as the linker, cells bound to the mouse antibody may be selectively separated.

Separating the target cells may include washing.

The method may further include detecting the separated target cells. Diseases including cancer may be diagnosed through the separated cells.

The compositions, kits, or methods according to embodiments of the present invention may be used to efficiently separate cells in a sample. Furthermore, detecting the separated cells may be used for diagnosing diseases.

BRIEF DESCRIPTION OF THE DRAWINGS

These and/or other aspects will become apparent and more readily appreciated from the following description of the embodiments, taken in conjunction with the accompanying drawings in which:

In FIGS. 2 and 3, the x-axis represents cell surface area coverage (%), whereas the y-axis represents types of antibodies.

DETAILED DESCRIPTION

Figure 1:
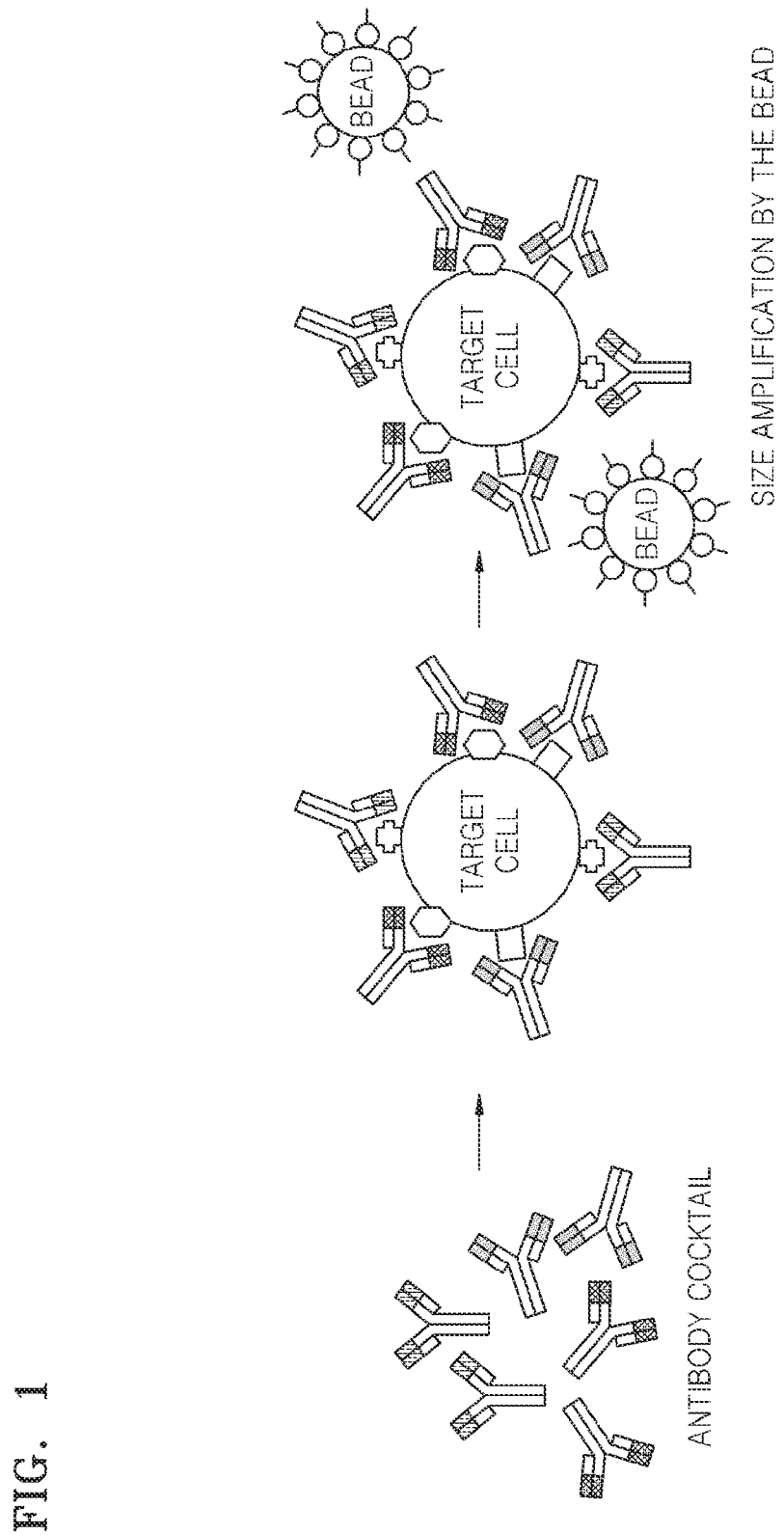
FIG. 1 is a schematic diagram showing a method of separating target cells using indirect binding according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Example 1

Comparing Bead Usage Using Monoclonal Antibodies to Bead Usage Using Polyclonal Antibodies First, the efficiency of bead-to-cell binding was determined using monoclonal antibodies. Beads were prepared by binding anti-EpCAM mouse IgG (R&D systems) to Dynabeads® Protein G (Invitrogen) to form a complex. 30 ul of the complex was incubated with MCF7 cells (EpCAM high expression cell line) or EMT (epithelial mesenchymal transition)-induced cells (EpCAM low expression cell line), and the cell surface area coverage (the proportion the entire surface area of the cell bound to beads) was determined.

Second, the efficiency of bead-to-cell binding was determined using polyclonal antibodies. In particular, the binding efficiency was determined for seven types of the antibodies that recognize cancer cell-surface proteins (anti-CD818 antibody (Abcam), anti-DDR1 antibody (Abcam), anti-FGFR antibody (Abcam), anti-Muc1 antibody (Abcam), anti-CAV1 antibody (Fitzgerald), anti-EGFR antibody (BD), and anti-EpCAM antibody (R&D systems)).

Figure 2:
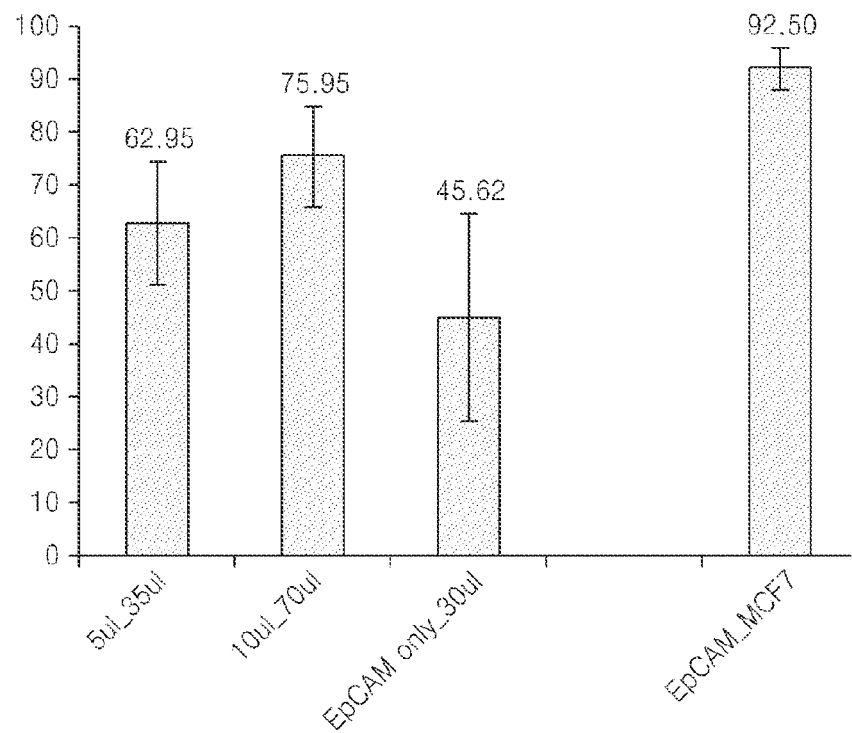
FIG. 2 is a graph showing the percent of cell surface area covered by beads for EMT-induced cells and MCF7 cells when monoclonal antibodies or polyclonal antibodies are used.

In FIG. 2, "5 ul_35 ul" represents adding 5 ul of each of the seven types of the antibody beads to EMT-induced cells, for a total of 35 ul, "10 ul_70 ul" represents adding 10 ul of each of the seven types of the antibody beads to EMT-induced cells, for a total of 70 ul, "EpCAM only_30 ul" represents singularly adding 30 ul of the anti-EpCAM antibody bead to EMT-induced cells, and "EpCAM_MCF7" represents singularly adding 30 ul of the anti-EpCAM antibody bead to MCF7 induced cells.

As illustrated in FIG. 2, coverage of EMT-induced cells was about 45.62%; however, coverage of MCF7 cells was about 92.50%. Accordingly, the binding efficiency of EMT-induced cells to the beads was comparatively lower than the binding efficiency of MCF7 cells to the beads. When beads bound to the seven types of antibodies were used, the coverage of EMT-induced cells was about 62.95%. When the amount of beads was doubled, the coverage of EMT-induced cells was increased about 75.95%.

Accordingly, for EMT-induced cells, the use of polyclonal antibodies resulted in higher binding efficiency than the use of monoclonal antibodies. The use of polyclonal antibodies may increase cell-to-bead binding efficiency, but may result in a decreased purity of separated target cells due to an increased amount of bead usage.

Example 2

Comparing Binding Efficiencies According to Methods of Direct Binding and Indirect Binding, and According to Types of Linkers 2-1. Comparing the Binding Efficiency of Direct Cell-to-Bead Binding to the Binding Efficiency of Indirect Cell-to-Bead Binding The binding efficiencies of EMT-induced cells were determined using direct binding and indirect binding.

In direct binding, a mouse antibody capable of recognizing an EpCAM protein overexpressed in MCF7 cells was bound to a bead, and then MCF7 cells and the bead were incubated to prepare a MCF7 cell-antibody-bead complex. In detail, 200 ug of anti-EpCAM antibody (R&D systems) was added to 1 ml of beads conjugated with protein G. The reactants were incubated at room temperature for one hour and refrigerated overnight. Thereafter, the reactants were washed three times using PBS. The reactants were blocked using a 5% (w/v) BSA, suspended in a 2% (w/v) BSA solution, and then refrigerated. The prepared anti-EpCAM antibody-bead and $5 \times 10^5$/ml of MCF7 cells were incubated at room temperature for about 30 minutes and the cell coverage was measured.

In indirect binding, MCF7 cells and an anti-EpCAM antibody were incubated. Then, the MCF7-anti-EpCAM complexes were incubated with beads bound to anti-mouse IgG. In detail, the bead was conjugated with a goat anti-mouse IgG and the reactants were washed with PBS. The reactants were blocked using a 5% (w/v) BSA, suspended in a 2% (w/v) BSA solution, and then refrigerated. Anti-EpCAM antibodies and $5 \times 10^5$/ml of MCF7 cells were incubated at room temperature and the bead was added into the reactant to prepare a MCF7 cell-antibody-bead complex. After preparing the complex, the cell coverage was measured.

Figure 3:
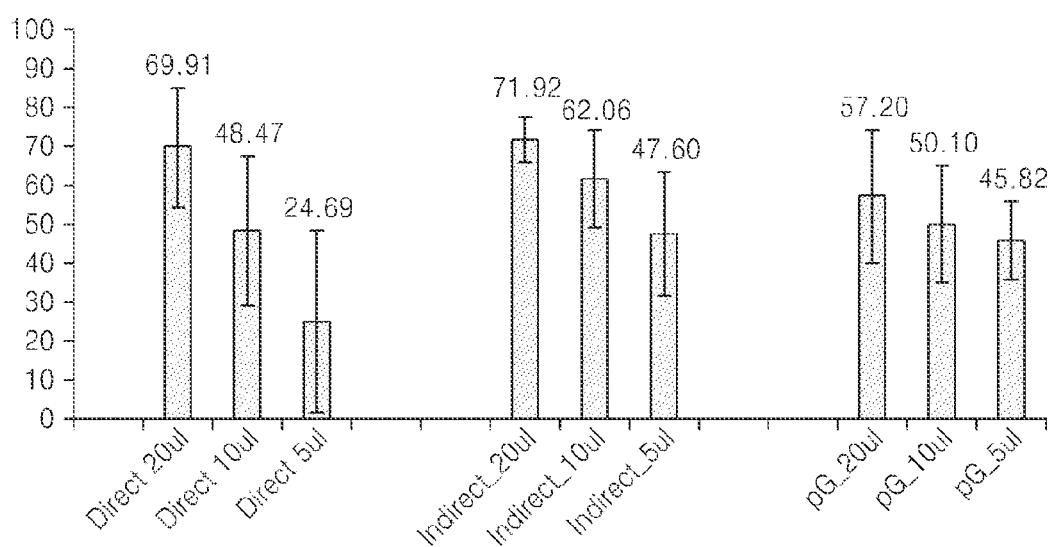
FIG. 3 is a graph showing the percent of cell surface area covered by beads for MCF7 cells using direct binding or indirect binding, and using different types of linkers for indirect binding.

In FIG. 3, "direct" refers to a direct binding between the mouse IgG and the bead, and "indirect" refers to an indirect binding between the mouse IgG, anti-mouse IgG, and the bead.

In direct binding, the MCF7 cells and a complex of the anti-EpCAM mouse IgG and the bead were incubated. When the MCF7 cells were reacted with 5 ul of the complex, the coverage was about 24.69%. The coverage increased as the amount of the complex increased.

In indirect binding, the MCF7 cells and the anti-EpCAM mouse IgG were incubated, and then the complex of the goat anti-mouse IgG and the bead was added to the incubated reactant and incubated. When the MCF7 cells were bound with 5 ul of the complex, the coverage was about 47.60%. The coverage increased as the amount of the complex increased.

When a cell coverage corresponding to the direct binding and a cell coverage corresponding to the indirect binding were compared, the cell coverage corresponding to the indirect binding was higher, which suggests that the indirect binding has a smaller amount of bead usage while showing an excellent coverage. Also, the direct binding showed an increased amount of bead usage and thereby a decreased purity, whereas the indirect binding showed a similar amount of bead usage as in when the monoclonal antibodies were used even when an amount of antibody usage increased, and the indirect binding also showed a decreased amount of bead usage and thereby an increased purity.

2-2. Comparing Cell Coverage According to Different Types of Linkers

In indirect binding, coverage (%) of MCF7 cells according to different types of linkers was determined.

When IgG was used as a linker, an anti-mouse IgG was conjugated to a dynal-protein G bead to form a complex. A cell-antibody complex was prepared by incubating a cell and an anti-EpCAM antibody. Then, the binding efficiency of the cell-bead binding was measured by adding about 5 ul to about 20 ul of bead—IgG complex to the cell-antibody complex.

When a protein G was used as the linker, protein G was conjugated to a dynal-protein G bead to form a complex. A cell-antibody complex was prepared by incubating MCF7 cells and an anti-EpCAM antibody. Then, the binding efficiency of the cell-bead binding was measured by adding the bead-protein-G complex to the cell-antibody-complex.

In FIG. 3, "indirect" refers to indirect binding between mouse IgG, anti-mouse IgG, and a bead, whereas "PG" refers to indirect binding between mouse IgG, protein G, and a bead.

As illustrated in FIG. 3, the binding efficiency between MCF7 cells and the bead using 20 ul of the complex of the anti-mouse IgG antibody bound to the bead was about 71.92%. In contrast, the binding efficiency between MCF7 cells and the bead using 20 ul of the complex of the protein G bound to the bead was about 57.20%.

Accordingly, in indirect binding, the cell-bead binding efficiencies varied according to the type of the linker used.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A method of separating cells, the method comprising:
   incubating a sample comprising target cells with two or more antibodies or antigen binding fragments thereof that specifically bind cell-surface proteins of the target cell, wherein the two or more antibodies or antigen binding fragments thereof are from two or more different host species, to prepare a first complex of a target cell and at least one of the two or more antibodies or antigen binding fragments thereof;
   incubating the first complex with a second complex comprising at least one anti-immunoglobulin antibody linker that specifically binds to an antibody or antigen binding fragment thereof of the first complex, wherein the at least one anti-immunoglobulin antibody linker is bound to a solid phase, and wherein incubating the first complex with the second complex provides a third complex comprising the target cell, the at least one antibody or the antigen binding fragment of the first complex, the anti-immunoglobulin antibody linker, and the solid phase, and
   separating the target cell from the third complex.

2. The method of claim 1, wherein each host species is a mouse, a rat, a rabbit, a goat, a guinea pig, or a human.

3. The method of claim 1, wherein the solid phase is a magnetic bead, a polystyrene plate, or a polystyrene bead.

4. The method of claim 1, wherein the cells are cancer cells, cancer stem cells (CSCs), circulating tumor cells (CTCs), cells that have undergone an epithelial mesenchymal transition (EMT), or a combination thereof.

5. The method of claim 1, wherein the method further comprises detecting the separated target cell.

* * * * *